United States Patent [19]

Bardy et al.

[11] Patent Number: 4,476,106

[45] Date of Patent: Oct. 9, 1984

[54] PROCESS FOR THE EXTEMPORANEOUS PREPARATION OF AN INJECTABLE FATTY ACID TAGGED IN THE OMEGA POSITION BY MEANS OF RADIOACTIVE IODINE

[75] Inventors: André Bardy, Morangis; Michel Comet, Saint Egreve; Sabine Coornaert, Dampierre; Jean-Paul Mathieu, Sassenage; Francoise Riché, Goncelin; Michel Vidal, Saint Ismier, all of France

[73] Assignee: Commissariat a l'Energie Atomique, Paris, France

[21] Appl. No.: 392,581

[22] Filed: Jun. 28, 1982

[30] Foreign Application Priority Data

Jul. 2, 1981 [FR] France ................................. 81 13039

[51] Int. Cl.$^3$ ...................... A61K 43/00; A61K 49/00
[52] U.S. Cl. ........................................... 424/1.1; 424/9
[58] Field of Search .................................. 424/1, 1.1, 9

[56] References Cited

U.S. PATENT DOCUMENTS 4,290,965 9/1981 Stocklin et al. .......................... 424/1
4,323,547 4/1982 Knust et al. ............................. 424/1

FOREIGN PATENT DOCUMENTS 0069948 1/1983 European Pat. Off. ................ 424/1
2947500 5/1981 Fed. Rep. of Germany .......... 424/1
2419265 10/1979 France ..................................... 424/1

OTHER PUBLICATIONS

Van Der Wall, Chem. Abstracts, 96, (1982), #208308w.
Freundlieb et al., Chem. Abstracts, 91, (1979), #188824c, 95, (1981), #78082j.
Machulla et al., Chem. Abstracts, 95, (1981), #80498t.
Knapp et al., J. Nucl. Med., 22, (1981), 988–993.
Journal of Nuclear Medicine, vol. 16, No. 1, Jan. 1975, G. D. Robinson et al., "Radioiodinated Fatty Acids for Heart Imaging: Iodine Monochloride Addition Compared with Iodine Replacement Labeling", pp. 17–21.

Primary Examiner—Christine M. Nucker
Attorney, Agent, or Firm—Pearne, Gordon, Sessions, McCoy, Granger & Tilberry

[57] ABSTRACT

A process for the preparation of a fatty acid tagged with radioactive iodine, wherein a brominated or iodized fatty acid is reacted, preferably in the omega position, with radioactive iodide in the dry state or with an aqueous solution of radioactive iodide, in the presence of vehicling iodide, to exchange the bromine or iodine of such fatty acid for radioactive iodine.

Application to use as radio-pharmaceutical products for studying cardiac metabolism troubles in human beings by scintigraphy.

20 Claims, No Drawings

PROCESS FOR THE EXTEMPORANEOUS PREPARATION OF AN INJECTABLE FATTY ACID TAGGED IN THE OMEGA POSITION BY MEANS OF RADIOACTIVE IODINE

The invention relates to a process for the extemporaneous preparation of an injectable fatty acid tagged or labeled in the omega position by means of radioactive iodine.

More precisely the invention relates to the preparation of fatty acids tagged with $I^{123}$ or $I^{131}$, which can be used as radio-pharmaceutical products for studying cardiac metabolism disturbances in human beings by scintigraphy.

BACKGROUND OF THE INVENTION

Of course, long-chain fatty acids form one of the main sources of energy of the cardiac muscle, and the metabolism of fatty acids tagged in the omega position by the radioactive isotopes $I^{123}$ and $I^{131}$ has proved to be very similar to that of natural fatty acids. As a result, a study of their myocardic capture opens up access to cellular functioning, so that tagged fatty acids have considerable advantage in nuclear medicine, all the more so since they also meet the criteria which they must possess and use as radio-pharmaceutical products. The fact is that tagging does not affect the biological properties of the molecule; the selection of $I^{123}$ as the tagging element meets biological and technical considerations, such as: short period of 6 to 20 hours and gamma emission of an energy of the order of 100 to 200 keV; moreover, the iodized or iodinated derivatives of fatty acids are not very toxic, and their capture rate is high.

However, their use in hospital services raises certain problems, since at present it is impossible to ensure the preparation of the tagged product at the moment when it is used in nuclear medicine laboratories.

Hitherto, in order to obtain fatty acids tagged with radioactive iodine, use was made of the Robinson method, in which the bromine of the brominated fatty acid to be tagged is exchanged for radioactive iodine (cf.Int. J. Appl. Radiat. Isot. Vol. 28, P. 149, 1977). As a rule the exchange reaction is carried out on brominated fatty acid in solution in butanone to which a solution of radioactive iodides (Na+, $I^{123}-$) has been added in the same solvent; exchange is performed by bringing the solution to reflux for 90 minutes or more. A preliminary study has shown that this method results in tagging yields which have poor reproducibility and are very often lower than 80%. In view of the low exchange yield, this technique, which uses a sequence of long, relatively complex operations, requires purification before the injection of the radio-pharmaceutical product.

To perform this stage of purification of the tagged acid, generally HPLC chromatography is used—i.e., a technique which cannot be routinely used in a nuclear medicine laboratory which has no specialized personnel. It is therefore impossible to prepare tagged fatty acid within the hospitals service.

It is precisely an object of the invention to provide a process for the preparation of a fatty acid tagged with radioactive iodine which results in a high tagging yield and therefore obviates the disadvantage of the prior art processes. In view of to the high tagging yield, there is no longer any need to use a very difficult purification stage to isolate the radio-pharmaceutical product before it is used. Thus, the tagged fatty acid can be prepared in the hot laboratory of a nuclear medicine service by non-specialist personnel.

BRIEF SUMMARY OF THE INVENTION

The invention provides a process for the preparation of a fatty acid tagged with radioactive iodine, wherein a brominated or iodized fatty acid is reacted, preferably in the omega position, with radioactive iodide in the dry state or with an aqueous solution of radioactive iodide, in the presence of vehicling or carrier iodide, to exchange the bromine or iodine of such fatty acid for radioactive iodine.

As a rule the exchange reaction is performed by heating for about 10 minutes at a temperature of about 102°-105° C., a solution of the brominated or iodized fatty acid in a water-miscible ketone containing the vehicling iodide formed, for example, by a metal iodide soluble in a ketone, such as sodium iodide, after the addition to the solution of radioactive iodide in the dry state or an aqueous solution of radioactive iodide. Operations are performed in a sealed flask, such as an antibiotics flask closed by a rubber membrane.

Preferably the radioactive iodide in the dry state or the aqueous solution of radioactive iodide has a pH of 7. When an aqueous solution of radioactive iodide is used, the solution preferably has a volumetric activity or specific concentration of at least 20 millicuries per cc.

When radioactive iodide is used in the dry state, it preferably has an activity such that the ratio between its activity in millicuries and the weight in milligrammes of the brominated or iodized fatty acid is at most 0.6.

Acetone or methyl ethyl ketone are examples of ketones which can be used.

The process as characterized above allows the reduction of the concentration of the oxidized forms of radioactive iodine in the tagging solution (molecular iodine or iodate ions) which, by reaction on the substrate or solvent, may lead to the formation of radioactive impurities on the one hand and to a reduction in the tagging yield on the other.

The fact is that although as a rule in exchange reactions it is preferable to avoid the presence of a non-radioactive iodide which takes part in the exchange reaction and therefore reduces the tagging yield, it has been found that in the process according to the invention advantage could be taken of the presence of such a vehicling or carrier iodide to improve the tagging yield. However, the concentration of cold iodide ions must be very high in face of that of the radioactive iodide ions and negligible in face of that of the halogenated fatty acid. As a rule a quantity of vehicling iodide is used such that the molar ratio between the iodized or brominated fatty acid and the vehicling iodide is $2 \times 10^2 \ldots$ to $10^6$.

The non-radioactive iodide ions play two essential roles:

In the conditions of the exchange reaction in a ketone medium and in the presence of water, the traces of oxidizing agents (molecular oxygen) cause the formation of oxidized forms of iodine ($I_2$, $IO_3 \ldots$) which immobilize part of the radioactive iodine. In contrast, if in the reaction medium the concentration of the radioactive iodide ions is very much lower than that of the cold iodide ions, the molar fraction of oxidized radioactive iodine will be negligible, and this results in an improvement of the tagging yield.

Although the reaction is performed in organic phase, the presence of traces of water enables disassociation equilibrium to be contemplated:

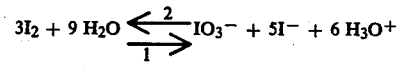

moreover, the iodide ions are in equilibrium with the $I_3^-$ ions:

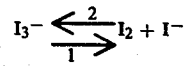

The addition of vehicling iodides or pushes such equilibria in the 2 direction, thus reducing the concentrations of the $IO_3^-$ and $I_2$ forms in the solution.

Similarly, it was found that the tagging yield is substantially improved by operating with iodide in the dry state with a pH of 7 or with an iodide solution of pH 7, rather than in a basic medium. This effect due to the reduction of the pH is certainly bound with a displacement of the disassociated equilibrium of the iodine in the 2 direction, causing a reduction in concentration of the iodate ions.

It should also be noted that the process according to the invention enables a tagging yield of at least 95% to be achieved, with relatively short exchange periods, as a rule not exceeding 5 to 7 minutes.

After the exchange reaction, the solvent is evaporated, with continuation of heating, after a venting needle has been introduced into the sealed flask. Then the resulting dry product is treated to bring it into a form which can be injected into the human body. To this end a slightly alkaline injectable buffer solution, for example, having a pH of about 9, such as a sodium carbonate buffer solution, is added; the result is a colloidal suspension of the tagged fatty acid which is dissolved in a liquid compatible with the human body, for instance, a solution of human albumin serum, or the blood serum of the patient to be examined.

The tagging process according to the invention therefore results in a radio-pharmaceutical product which can be injected directly without requiring complex, lengthy operations, since the duration of all the operations of tagging and of conversion of the tagged product into an injectable solution does not exceed 30 minutes; these operations can be performed by non-specialist personnel in the hot laboratory of a hospital service at the moment of use.

In this case, the reagents used were first purified to make them sterile and apyrogenic. To facilitate operations, the various reagents, except for the solution of radioactive iodide, are conditioned in flasks each containing the necessary quantities for the preparation of the dose of radiopharmaceutical product to be injected. The flasks are then stored in a case, so as to have for each operation all the necessary reagents which have been subjected to the required checks, and which remain stable for several months.

In this way the expenses of each scintigraphic examination can be limited, since the checking and purification operations are less burdensome when they are performed on a lot of products conditioned in a case, rather than on each dose of tagged product.

The case comprises a compartmentalized support receiving a series of flasks such:

a first flask containing a crystallized fatty acid,
a second flask containing a ketone and a vehicling iodide,
a third flask containing a slightly alkaline injectable buffer solution, and
a fourth flask containing human albumin serum.

In a preferred embodiment of the invention, the exchange reaction is performed starting from the iodized derivitive of the fatty acid to be tagged.

In this way the speed of the exchange reaction is increased, since iodine is a better nucleophilic group and therefore a complete reaction can be obtained after about 5 minutes. Moreover, the fact of starting from the iodized derivative enables a homogeneous product to be obtained and avoids the injection of brominated derivative and subsequently the formation in vivo of bromoacetate, which is toxic.

The derivitives of long-chain fatty acids, iodized or brominated in the omega position, can be obtained by a tosylation reaction of the hydroxy omega fatty acids, followed by a $TsO^-$, $X^-$ exchange reaction.

When the hydroxy omega fatty acids do not exist in the natural state, they can be obtained either from natural trihydroxy acids, by elimination reaction, or by the condensation of a short-chain omega brominated acid on a true acetylenic alcohol, resulting in an acetylenic omega-hydroxy acid which is then reduced to obtain the ethylenic derivative or the saturated compound.

By way of example, 16 hydroxy-9-hexadecenoic acid can be obtained from aleuritic acid, which exists in the natural state, as described by D. E. Ames, T. G. Goodburn, A. W. Jevans and J. F. McGhie J.Chem.Soc.(C), 268, 1968.

The conversion of 9,10,16-trihydroxy hexadecenoic acid into E or Z 16-hydroxy-9-hexadecenoic acid is performed by the action of phosphonium iodide on the diasteroisomers of aleuritic acid, followed by alkaline hydrolysis.

However, when the aformentioned method is used, the reaction yields are relatively low. It is therefore preferable to perform the total synthesis of the fatty acids halogenated in the omega position by the condensation of a short-chain omega brominated acid on an acetylenic alcohol. This method offers many possibilities both as regards the length of the chain and the position of unsaturation. The selection of omega brominated acid and acetylenic alcohol also enables several triple or double links to be introduced into the hydrocarbonated chain.

The invention provides a process for the preparation of an iodized fatty acid having the formula:

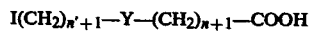

where Y denotes the links $-CH_2-CH_2-$ or $-CH=CH-$ Z or E, and n and n' are integers from 3 to 10, wherein a brominated omega acid having the formula:

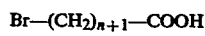

and an acetylenic alcohol having the formula:

are condensed in liquid ammonia in the presence of lithium amide to obtain hydroxy omega alkynoic acid having the formula:

HO—(CH$_2$)$_{n'+1}$—C≡C—(CH$_2$)$_{n+1}$—COOH, and then the omega-hydroxy-alkynoic acid is subjected to reduction to obtain the corresponding omega-hydroxy-alkenoic acid or hydroxy alkanoic acid, the omega-hydroxy-alkenoic acid or the omega-hydroxy-alkenoic acid thus obtained is reacted with paratoluene sulfonyl chloride to obtain the corresponding tosylated derivative, and the tosylated derivative thus obtained is subjected to a tosylate-iodine exchange reaction to obtain the corresponding iodized derivative.

In a variant of the process, an iodized fatty acid is prepared having the formula:

I(CH$_2$)$_{n'+1}$—C≡C—(CH$_2$)$_{n+1}$—COOH where n and n' are integers from 3 to 10, by subjecting omega-hydroxy-alkynoic acid directly to the tosylation and exchange reactions.

The following reaction diagram sums up the different stages of these processes of synthesis:

Br—(CH$_2$)$_{n'}$—COOH $\xrightarrow{\text{H—C≡C—Na, NH}_3}$

H—C≡C—(CH$_2$)$_{n'}$—COOH and by reduction of the carboxy group of the acid obtained by treatment with diazomethane followed by a reduction in ether, in accordance with the following reaction equation:

H—C≡C—(CH$_2$)$_{n'}$—COOH $\xrightarrow[\text{(2) LiAlH}_4]{\text{(1) CH}_2\text{N}_2}$ H—C≡C—(CH$_2$)$_{n'}$—CH$_2$OH The omega-bromo alkanoic acids used as the starting products for the synthesis can be obtained by reaction of 1 omega-dibromo-alkane on the sodium derivative of ethyl malonate, resulting in the di-condensation and mono-condensation products, the latter being isolated by distilling the reaction mixture under reduced pressure.

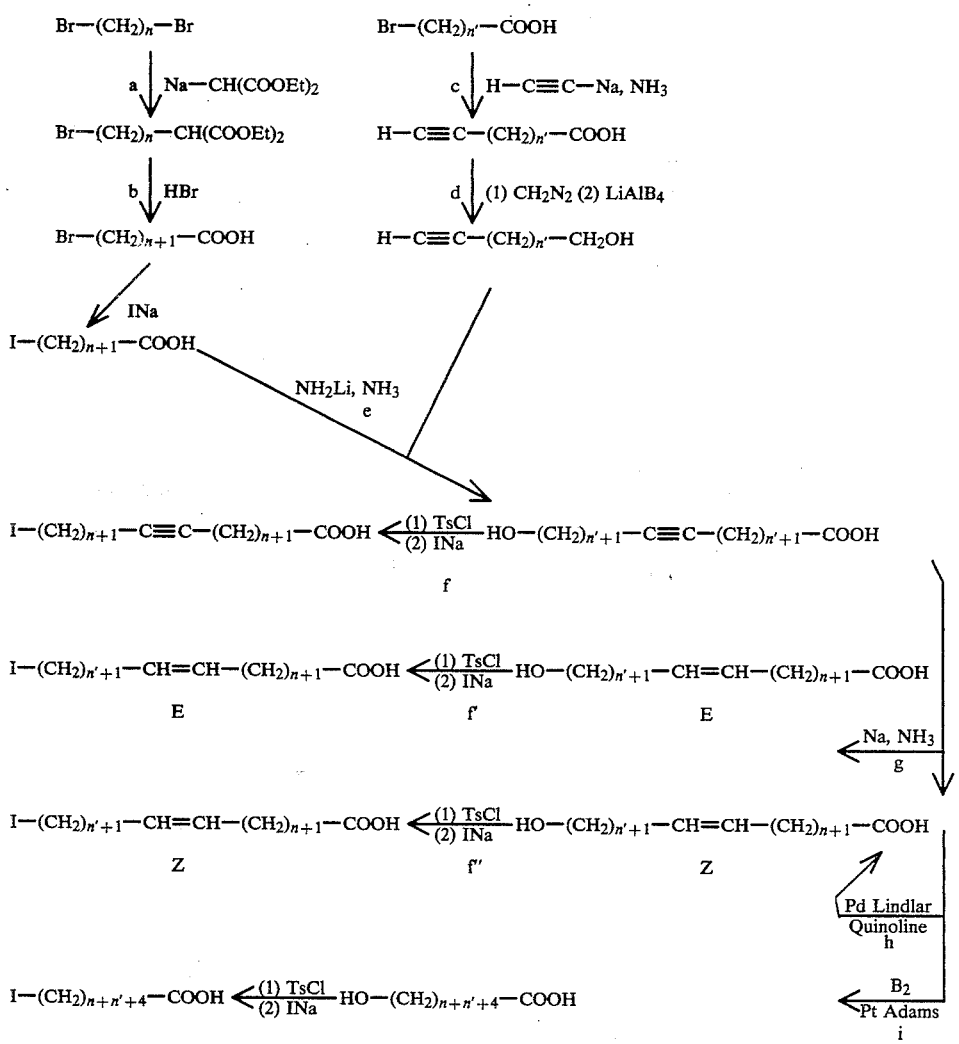

The true acetylenic alcohol used as a starting product for this synthesis can be prepared by the nucleophilic substitution of the acetylide ion on the salt of a bromo-omega alkanoic acid in liquid ammonia, in accordance with the following reaction equation:

Br—(CH$_2$)$_n$—Br $\xrightarrow{\text{NaCH(COOEt)}_2}$

-continued

Br—(CH$_2$)$_n$—CH(COOEt)$_2$ +

(EtOCO)$_2$CH—(CH$_2$)$_n$—CH(COOEt)$_2$ + NaBr followed by decarboxylation in an acid medium (HBr) of the ethyl omega-bromoalkyl malonate to produce omega-bromo-alkanoic acid, by the following equation:

Br—(CH$_2$)$_n$—CH(COOEt)$_2$ $\xrightarrow{\text{HBr/H}_2\text{O}}$ Br—(CH$_2$)$_{n+1}$—COOH The (e) condensation reaction of an omega-brominated acid and of a true acetylenic alcohol to form a omega-hydroxy-alkynoic acid is carried out in liquid ammonia in the presence of lithium amide. Lithium is selected because that metal blocks the OH function: the reaction of the brominated acid on the di-lithium derivative of the acetylenic alcohol causes no O-alkylation; only C-alkylation is observed. The acetylenic alcohol must be used in considerable excess in relation to the brominated acid (3 to 10 moles to 1 mole), since the speed of the condensation reaction being very low at $-35°$ C., there is a risk of the duplication of the brominated acid or the formation of amine.

The omega-hydroxy-alkynoic acid obtained is then subjected to partial or total reduction to form the corresponding omega-hydroxy-alkenoic or alkanoic acid, which can then be converted by tosylation and iodization of the terminal hydroxy group, into saturated iodized acid or Z or E ethylenic acid:

to obtain the omega-hydroxy-alkanoic acids, the omega-hydroxy-alkynoic acids are completely hydrogenated. The catalyst used is Adams platinum (PtO$_2$) and the reaction is carried out either in acetic acid, or in an alcohol such as propanol, or in ether, to obtain the Z omega-iodo-alkenoic acid, a partial and highly sterioselective catalytic hydrogenation is performed of the omega-hydroxy-alkynoic acids by means of the Lindlar catalyst (a catalyst with 5% palladium on calcium carbonate deactivated at 95° C. by a lead acetate solution) in the presence of quinoline.

To obtain the E omega-iodo-alkenoic acids, stereospecific reduction of the omega-hydroxy-alkynoic acids is performed chemically; the reducing agent used is sodium in solution in liquid ammonia under pressure at a temperature of 20°-60° C.

The hydroxylated fatty acids in the omega position are then subjected to the tosylation and exchange reactions (f, f′, f″ or f‴) to obtain the iodized fatty acids in the omega position.

The tosylation reaction is performed in pyridine or in a solvent such as dichloromethane. To avoid elimination, in all cases the reaction is performed at low temperature: between 0° and 5° C. The reaction time varies from 2½ to 24 hours when pyridine is used as the solvent, while it is eight days if dichloromethane is used.

Preferably, therefore, the reaction is performed in pyridine, using a slight excess of paratoluene sulfonyl chloride over the alcohol.

The exchange reaction is an attack by the tosylate, which is a very good starting group, by the nucleophilic I$^-$ ion.

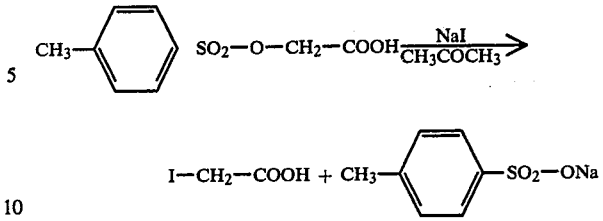

The tosylate-iodine exchange reaction is comparable to the bromine-iodine exchange, taking place in acetone with reflux by the Gensler and Thomas method and it must be performed under a nitrogen atmosphere.

Before being used in the process according to the invention, the iodized or brominated derivatives are purified by high-performance liquid chromatography, using a silica-based support and an elution agent mainly formed by heptane, ether and acetic acid. Generally, for this purification stage use is made of an HPLC chromatograph having a differential refractometer and one or two Prep Pak 500 type silica columns, elution being performed by means of a mixture of 97.8% heptane, 1.8% ether and 0.4% acetic acid with a flow rate of 200 cc per minute, at a pressure of 5 bars, injecting a 3-5 g sample.

The purification performance can be enhanced by mounting two silica columns in series and increasing the polarity of the solvent, formed in this case by a mixture of 95.6% heptane, 4% ether and 0.4% acetic acid with a flow rate of 50 cc per minute and a pressure of 8 bars. After the purification stage, the iodized or brominated derivative is subjected to sterilization and then conditioned in flasks.

Other advantages and features of the invention will be gathered from the following non-limitative, purely illustrative examples.

EXAMPLE 1

Preparation of iodized fatty acids in the omega position (1) Preparation of the acetylenic alcohols
(a) Preparation of omega-alkynoic acid

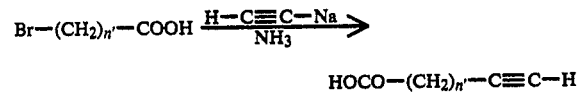

HOCO—(CH$_2$)$_{n'}$—C≡C—H 40 g of Na was dissolved, with continuous agitation, in a tricol containing 2 l of liquid ammonia under a flow of acetylene. Acetylene was added until the blue colour of the sodium in solution completely disappeared. Then 0.49 mole of omega-bromo-alkanoic acid was added in solution in 150 cc of THF, and then 150 cc of pure THF was added. The mixture was agitated for 15 hours until the ammonia had completely evaporated. The precipitate was recovered with a little ether and hydrolyzed. The reaction mixture was acidified (HCl 11N) and the product was extracted with ether. The ethereal phase was washed in water, filtered on Whatman phase-separating paper, and evaporated. The product was distilled under reduced pressure.

7-Octynoic acid (n′=5): H—C C—(CH$_2$)$_5$—COOH
Eb$_{0.6}$=95°-100° C., yield 65%

8-Nonynoic acid (n′=6): H—C C—(CH$_2$)$_6$—COOH
Eb$_{0.5}$=106°-108° C.; yield 65%

(b) Conversion of the acid into acetylenic alcohol

Diazomethane in solution in ether was added to the compound obtained under (a), until the yellow colouring persisted. The excess diazomethane was destroyed by a few drops of acetic acid. The volume of ether was brought to 200 cc by evaporation. Then 0.3 mole of ester was obtained, because the esterification yield is practically quantitative.

In a 2 l round-bottom flask with three necks, adapted with a condenser, a bromine ampulla and an agitator, 11.4 g of LiAlH$_4$ was put in suspension in 500 cc of anhydrous ether, and the mixture was kept at 0° C. The ester in solution in ether (0.3 mole in 200 cc) was added drop by drop and agitation was continued for 2 hours (0° C.). The solution was then hydrolyzed with 80 cc of NaOH 5N (up to flocculation). The solid phase was washed with ether. The ethereal phase was washed with a saturated ammonium chloride solution filtered on Whatman phase-separating paper; the ether was evaporated and the residue dried by azeotropic distillation (benzene) and distilled under reduced pressure.

7-Octynol 1: $Eb_{0.6}=74°$ C.; yield 65%

8-Nonynol 1: $Eb_{0.6}=85°$ C.; yield 90%

(2) Preparation of omega-brominated acid (a) Preparation of ethyl omega-bromo-alkyl malonate

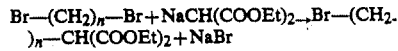

In a tricol fitted with a reflux condenser, a bromine ampulla and an agitator, 0.45 mole (10.35 g) of Na were dissolved in 140 cc of absolute ethanol distilled over magnesium. 0.90 mole (133.2 g) of distilled ethyl malonate ($Eb_{15}=102°$ C.) was added slowly to the cooled solution (20° C.). The mixture was heated for 1 hour at 60° C. on a water bath and then cooled to 0° C. Then 0.49 mole of 1-omega-dibromo-alkane dissolved in 98 cc of anhydrous ether was slowly added. The reaction mixture was left for 3 days at ambient temperature. The ether and ethanol were evaporated and the residue, mixed with 200 cc of water, was extracted B 4 times with 250 cc of ether. The ethereal phase was washed with water, filtered on Whatman phase-separating paper, and dried on Na$_2$SO$_4$. The ether was evaporated and the reaction products distilled under reduced pressure. The following fractions were collected:

Ethyl (5-bromopentyl) malonate

Br—(CH$_2$)$_5$—CH(COOEt)$_2$

1: Ethyl malonate CH$_2$(COOEt)$_2$: $Eb_1=64°$ C.

2: Dibromopentane Br—(CH$_2$)$_5$—Br: $Eb_1=74°$ C.

3: Ethyl (5-bromopentyl) malonate

Br—(CH$_2$)$_5$—CH(COOEt)$_2$: $Eb_1=154°$ C.; yield 43%

4: Tetraester (EtOCO)$_2$CH—(CH$_2$)$_5$—CH(COOEt)$_2$: $Eb_1 > 160°$ C.

Ethyl (6-bromohexyl) malonate

Br—(CH$_2$)$_6$—CH(COOEt)$_2$

1: Ethyl malonate: $Eb_{13}=95°$-$100°$ C.

2: Dibromohexane Br—(CH$_2$)$_6$—Br: $Eb_{13}=90°$ C.

3: Ethyl (6-bromohexyl) malonate

Br—(CH$_2$)$_6$—CH(COOEt)$_2$: $Eb_{0.3}=139°$ C., $n_D^{20}=1.460$, yield 41%

4.: Tetraester of dicarboxysebacic acid (EtOCO)$_2$—CH—(CH$_2$)$_6$—CH(COOEt)$_2$: $Eb_{0.3} > 139°$ C.

Ethyl (10-bromodecyl) malonate

Br—(CH$_2$)$_{10}$—CH(COOEt)$_2$

1: Ethyl malonate: $Eb_1=64°$ C.

2: Dibromodecane Br—(CH$_2$)$_{10}$—Br: $Eb_1=150°$ C.

3: Ethyl (10-bromodecyl) malonate

Br—(CH$_2$)$_{10}$—CH(COOEt)$_2$: $Eb_1=192°$ C. yield 61%

4: Tetraester (EtOCO)$_2$CH—(CH$_2$)$_{10}$—CH(COOEt)$_2$: $Eb_1=195°$ C.

(b) Conversion to omega-bromo-alkanoic acid

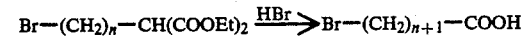

0.18 Mole of malonic derivative and 51 g of 48% HBr were heated in water in a tricol having a bromine ampulla and a distillation column with a descending condenser. The reaction mixture was heated to 120°-150° C. The ethyl bromide distilled at the top with water and HBr. As distillation continued, a quantity of hydrobromic acid equal to that of the distillate collected (150 cc in all) was added in the tricol. The mixture was heated for 4 hours. After cooling the product was hydrolized with ice and 250 cc of water.

The acid precipitated in the solid state and was extracted with ether (500 cc). The ethereal phase was washed once with water and evaporated. Finally, the crude acid was dried by azeotropic distillation ($\phi$H) and distilled under reduced pressure:

7-bromoheptanoic acid Br—(CH$_2$)$_6$—COOH: $Eb_{0.8}=124°$ C.; yield 74%

8-bromooctanoic acid Br—(CH$_2$)$_7$—COOH: $Eb_{0.8}=142°$ C.; yield 67.5%

12-bromododecanoic acid Br—(CH$_2$)$_{11}$—COOH: $Eb_{0.8}=174°$ C.; yield 30.5%

(3) Preparation of omega-hydroxy-alkynoic acid

The reaction was performed in a tricol having mechanical agitation, a bromine ampulla and a dried ice, acetone condenser ($-80°$ C.). 0.124 mole of acetylenic alcohol in solution in 100 cc of anhydrous THF (over 30 minutes) were added to 0.32 mole of lithium amide (obtained by the reaction of 2.24 g of Li in the presence of ferric nitrate) in solution in 1.5 l of liquid ammonia. Agitation continued for 45 minutes after the completion of the addition. 0.048 mole of omega-bromoalkanoic acid was added in solution in 200 cc of anhydrous THF. The reaction mixture was kept agitated for 20 hours. After the evaporation of the ammonia, the mixture was hydrolyzed by the addition of ice. The pH of the solution was brought to 3 (HCl 11N) and the acid was extracted with ether, then dried by azeotropic distillation (benzene). It was recrystallized in an ether-pentane mixture.

| | Yield | F° C. | Elemental analysis | | | |
|---|---|---|---|---|---|---|
| | | | C | | H | |
| | | | calculated | obtained | calculated | obtained |
| 14-Hydroxy 7-tetradecynoic acid | 60% | 38–41 | 70.0 | 69.85 | 10.0 | 10.11 |

-continued

| | Yield | F° C. | Elemental analysis | | | |
|---|---|---|---|---|---|---|
| | | | C | | H | |
| | | | calculated | obtained | calculated | obtained |
| (n = 4, n' = 5) 16-Hydroxy 9-hexadecynoic acid | 76% | 60–62 | 71.64 | 71.74 | 10.45 | 10.40 |
| (n = 6, n' = 5) 20-Hydroxy 12-eicosynoic acid | 63.5% | 77–79 | 74.07 | 73.46 | 11.11 | 11.18 |
| (n = 9, n' = 6) | | | | | | |

(4) Partial catalytic hydrogenation to Z omega-hydroxy-alkenoic acid

Hydrogenation was performed in an apparatus comprising a hydrogen reserve, a hydrogenation enclosure and a vacuum device. $3.7 \times 10^{-3}$ mole of omega-hydroxy-alkynoic acid and 450 mg of quinoline were dissolved in an Erlenmeyer flask containing 40 cc of propanol or ether.

Then 150 mg of Lindlar catalyst was added and the Erlenmeyer flask was attached to the hydrogenation enclosure. After the enclosure had been surged, agitation was started and the hydrogen consumption was measured as a function of time, at ordinary pressure. When hydrogenation was completed, the solution was filtered, the propanol evaporated, and the residue placed in 100 cc of ether which was washed twice with acidulated water (HCl) and twice with water. The ethereal phase was filtered on Whatman phase-separating paper and then evaporated. The product was analyzed. The two Z ethylenic acids synthesized (to $C_{14}$ and $C_{16}$) were liquid at ordinary temperature. The yields were of the order of 80%.

(5) Total hydrogenation to omega-hydroxy-alkanoic acid

The method of operation was identical with the preceding one. The reaction was carried out on $3.7 \times 10^{-3}$ mole of omega-hydroxy-alkanoic acid in the presence of 20 mg of $PtO_2$. The products were recrystallized in acetone. The yields were 70 to 80%.

(6) Partial hydrogenation to E omega-hydroxy-alkenoic acid

The omega-hydroxy-alkynoic acid ($3.7.10^{-3}$ mole) was dissolved in 50 cc of anhydrous ether and poured into an autoclave of 500 cc. The whole was cooled to $-50°$ C. (using acetone and dry ice). Then 2 g of sodium dissolved in 150 cc of liquid ammonia was added. The autoclave was closed and agitated for one day in a water bath at $57°$ C. The remaining ammonia was evaporated and the reaction mixture hydrolyzed (ice and water). The medium was acidified (HCl 11N) and the product extracted with ether. The ethereal phase was washed with water, filtered on Whatman phase-separating paper, and evaporated. The product was analyzed. Yield 50 to 60%.

(7) Tosylation of omega-hydroxy acid $3.6 \times 10^{-3}$ mole of omega-hydroxy acid was dissolved in 6 cc of pyridine. The solution was kept agitated at $0°$ C. 0.86 g ($4.5 \times 10^{-3}$ mole) of paratoluene sulfonyl chloride was added in portions. Agitation continued for 8 hours, then the whole was kept at $5°$ C. for 10 to 48 hours. The reaction was followed by thin-layer chromatography (elution agent: ether, pentane 7/3, support $SiO_2$, revelation by heating of the plate after pulverization with a 1% cobalt chloride solution in $H_2SO_4$ at 10%). The reaction medium was hydrolyzed by the slow addition of 1 cc of water and then the quicker addition of 6 cc of water. The tosylate of the fatty acid was then extracted by $CH_2Cl_2$, and recrystallized in pentane at $-20°$ C.

(8) Iodization of the fatty acid tosylate

The iodization reaction of the fatty acid tosylate was performed in a nitrogen atmosphere. The preceding tosylate was dissolved in 20 cc of acetone and 2.2 g ($14.8 \times 10^{-3}$ mole) of NaI were added. The reaction mixture was refluxed for two hours. The solution was filtered, the acetone evaporated, and the product was added to 100 cc of ether. The ethereal phase was washed twice with 50 cc of water with the addition of sodium metabisulphite ($Na_2S_2O_5$, 20%) then evaporated.

The product was dried by azeotropic distillation (acetone) and then recristallized in pentane at $-20°$ C. It was then analyzed:

Z 14-iodo-7-tetradecenoic acid:
F<$20°$ C.
14-Iodotetradecanoic acid:
F=$65°$–$67°$ C.

The iodized fatty acids in the following Table were obtained in the same way.

| No. | | F° C. | Yield in relation to the hydroxylated derivative | Elemental analysis | | | | | |
|---|---|---|---|---|---|---|---|---|---|
| | | | | C | | H | | I | |
| | | | | Calculated | Obtained | Calculated | Obtained | Calculated | Obtained |
| 1 | 16-iodo-9-hexadecynoic acid | 35–37 | 29 | 50.79 | 51.07 | 7.14 | 7.30 | 33.59 | 31.18 |
| 2 | 20-iodo-12-eicosynoic acid | 46–50 | 22 | 55.29 | 57.71 | 8.06 | 8.46 | — | — |
| 3 | 16-iodo-9-hexadecenoic acid | 49–51 | 39 | 50.53 | 50.20 | 7.63 | 7.80 | 33.42 | 30.42 |
| 4 | 16-iodo-hexadecanoic acid | 65–67 | 20 | 50.26 | 51.46 | 8.11 | 8.22 | 33.24 | 30.96 |
| 5 | 20-iodoeicosanoic acid | 79–80 | 25 | 54.79 | 54.85 | 8.88 | 9.08 | 28.99 | 26.34 |

EXAMPLE 2

This Example illustrates the preparation of E 16-iodo-9-hexadecenoic acid by means of $I^{123}$.

In this example 1.4 cc of acetone containing 3.5 μg of sodium iodide were added to a flask containing a certain amount of crystallized fatty acids; then the contents of the flask were added to another flask containing 35 microliters of sodium iodide 123, representing an activity of 1 millicurie; then the flask was heated in a dry water bath at 103° C. for 5 minutes.

On completion of the operation, the tagging yield was determined by electrophoresis in a Veronal medium at 200 volts for 30 minutes to make the iodide ions migrate, and by the counting of the peaks of radioactivity on the various zones of the electrophoresis paper. The following Table gives the results obtained when tagging is performed with different amounts of fatty acid.

| Starting iodized fatty acid (in mg) | Amount of INa per mg of fatty acid | Amount of $I^{123}$ per mg of fatty acid | Yield |
|---|---|---|---|
| 2 mg | 1.75 μg | 500 μCuries | 92.1% |
| 3 mg | 1.17 μg | 333 μCuries | 91.9% |
| 3.5 mg | 1 μg | 285 μCuries | 95.8% |

The Table shows that very satisfactory results are obtained with 285 millicuries of radioactive iodine per gram of fatty acid.

EXAMPLE 3

This example illustrates the influence of the pH of the radioactive iodide solution on the results obtained. 2 mg of 16-iodo-9-hexadecenoic acid were dissolved in 2 cc of acetone containing 5 microgrammes of sodium iodide, and the solution obtained was added to 40 microliter of radioactive sodium iodide solution having a total activity of 1 millicurie, the whole then being heated at 103° C. in a dry water bath for 5 minutes.

On completion of this operation, the tagging yield was determined by electrophoresis and by counting as before. When an iodide solution with a pH of 12.3, was used, the tagging yield was 85.2%, while with the use of an iodide solution with a pH substantially equal to 7, the tagging yield is 93.3%. It is therefore observed that the use of an iodide solution with a pH of 7 enables the tagging yield to be appreciably increased.

EXAMPLE 4

This example illustrates the influence of the volumetric activity on the results obtained of the aqueous solution of radioactive iodide and of the volumes of iodide solution and fatty acid solution used.

In this example, for tagging a solution was used comprising 2.5 mg/cc of 16-iodo-9-hexadecenoic acid in acetone containing vehicling or carrier sodium iodide with a fatty acid/vehicling or carrier iodide molar ratio of $4 \times 10^2$. A certain amount of aqueous solution of radioactive sodium iodide was added to the acetone solution containing the fatty acid, and then the whole was heated to a temperature of 102°–104° C. in a dry water bath for 5 minutes. On completion of this operation the tagging yield was determined by chromatography on DOWEX AG-1 X8 anionic resin, form Cl−: the resin was conditioned under acetone, an equal quantity of the tagging solution placed on the resin was eluted by this solvent, the iodides were retained, and the radioactive fatty acid was eluted;

$$\text{Tagging yield} = \frac{\text{activity of the eluate}}{\text{activity of eluate + activity od resin}}$$

The results obtained for different volumes of fatty acid solution in acetone and radioactive sodium iodide solution are given in the accompanying Table I.

These results are confirmed by CMC (support cellulose, elution agent: heptane: 380 V, ether: 80 V, acetic acid IV). The Rf of the fatty acid lies between 0.9 and 1, that of the ionic species differing little from 0. The cellulose bands corresponding to Rf (0-0.2), . . . (0.8-1) were recovered and their radioactivity measured.

$$\text{Tagging yield} = \frac{Rf \text{ radioactivity (0.8 to 1)}}{\text{Total radioactivity}}$$

The quality of the tagged product is checked by analytical HPLC, using the following conditions:
steady phase, $SiO_2$ (10 μm)
elution agent: heptane 98.1% ether 1.5% acetic acid 0.4%
flowrate: 7 cc/minute The column was first conditioned, using a n-heptane solution containing 3% acetic acid.

The crude tagging solution was analyzed by the following method: the acetone of the tagging solution was evaporated (without loss of radioactivity); the tagged fatty acid, analyzed in solution in the elution agent, led to a single radioactive product which absorbed UV radiation (7.5 volumes of column). Studied in NMR $^1$H, the product has the characteristics of the initial iodized fatty acid. In all the cases studied, HPLC analysis reveals no impurities (>1%) which are radioactive or absorbant in the UV.

Moreover, it should be noted that it is impossible to analyze the tagging solution in acetone directly, for the following reasons: the acetone often contains impurities which absorb UV; and it seems that the fatty acid and this solvent lead to separate associations in HPLC.

Table I shows that the best results are obtained when use is made of a volume of sodium iodide solution of 80 microliters, representing a total activity of 2 millicuries, and a volume of fatty acid solution 2.8 milliliters, having a fatty acid concentration of 2.5 mg/ml, and a concentration of vehicling or carrier iodide such that the fatty acid/vehicling or carrier NaI molar ratio is $4.10^2$.

It has also been found that periods of heating greater than 5 minutes had no effect on the tagging yield.

Lastly, it may be deduced from these results that the volumetric ratio between the fatty acid solution and the $NaI^{123}$ solution must be at least 14.

EXAMPLE 5

In this example we study the influence of the volumetric ratio between the aqueous solution and the fatty acid solution on the tagging yield, in this case the $I^{131}$ tagging of 16-iodo-9-hexadecenoic acid.

In this case the same operational method was followed as in example 4. The results obtained are given in the adjoining Table II, which also states the conditions used.

EXAMPLE 6

This example illustrates the preparation of an injectable fatty acid solution tagged with $I^{123}$ by the process according to the invention.

Each of the constituents required for tagging and for obtaining an injectable solution was conditioned in a sterile and apyrogenic manner in a "penicillin" type flask. The flasks, which were prepared beforehand and subjected to all the necessary checks for their use in medicine, were disposed in a case which therefore comprised:

a flask A containing 7 mg of crystallized 16-iodo-9-hexadecenoic acid, a flask B containing acetone and sodium iodide, a flask C containing 5 cc of buffer solution with a pH of 9 and having the the following composition:
0.28 mg of anhydrous sodium carbonate, and
1.6 mg of sodium bicarbonate per cc of sodium chloride solution (9 for 1000)

a flask D containing human albumin in 20% solution in physiological serum.

For tagging, a flask was also used containing the necessary amount of aqueous solution of radioactive iodide, which was delivered at the last moment. The flask contained 40 microliters of aqueous solution of sodium iodide with a pH of 7 and having a total $I^{123}$ activity of 1 millicurie.

To perform the tagging, from flask B 2.8 cm$^3$ of acetone was taken containing 7 µg of sodium iodide, and then added to the contents of flask A—i.e., to the 7 mg of crystallized fatty acid—the result being a solution of the fatty acid in acetone containing the required quantity of vehicling or carrier sodium iodide.

1.4 cm$^3$ of the solution was then taken from flask A and added to the flask sealed by a rubber membrane and containing the radioactive iodide solution with a pH of 7. The sealed flask containing the radioactive iodide solution and the fatty acid solution was then placed in a dry water bath and heated at a temperature of 102°–103° C. for 5 minutes to perform the exchange reaction and obtain the fatty acid tagged by $I^{123}$. After heating, a venting needle was introduced into the rubber membrane closing the flask, so as to eliminate the acetone by evaporation. After that operation, from flask C 3 cc of the buffer solution was taken and introduced into the flask containing the tagged fatty acid; then the latter was placed in a dry water bath, subjecting the contents to agitation and heating for about 15 minutes at 70° C. to obtain a colloidal suspension of tagged fatty acid. When the suspension had cooled a little, 1 cc of human albumin serum was added which was taken from flask D, the solution then becoming limpid: the solution of iodized fatty acid tagged with $I^{123}$ thus obtained was directly injected intravenously.

EXAMPLE 7

This example illustrates the preparation of an injectable solution of fatty acid tagged with $I^{123}$ by the process according to the invention, but using the radioactive iodide in the dry state, instead of an aqueous solution of radioactive iodide.

The radioactive iodide in the dry state was obtained by the evaporation of an aqueous solution of radioactive $I^{123}$ produced in a cyclotron and delivered at a pH of 7 with an activity of 10 millicuries per milliliter. To convert that solution into dry radioactive iodide, a volume equal to the required activity and calibrated for the hour of use was introduced into a penicillin-type delivery flask. Then the flask was heated in a dry thermostated bath at 100° C. without the plug and evaporated to dryness. Then the flask was plugged, set and subjected to sterilization in the autoclave for 20 minutes at 120° C.

The constituents required for tagging are in a case comprising, as in example 6, a flask A containing 7 mg of crystallized 16-iodo-9-hexadecenoic acid, a flask B containing acetone and sodium iodide, a flask C containing 5 cc of the buffer solution with a pH of 9, and a flask D containing human albumin in 20% solution in physiological serum.

For tagging, use was also made of a flask containing the necessary activity in radioactive iodide in the dry state which was delivered at the last moment. The flask contained 4 millicuries of radioactive iodide with a pH of 7 in the dry state.

To perform the tagging, 1 cc of acetone containing 2.5 µg of sodium iodide is taken from flask B and added to the contents of flask A—i.e., to the 7 mg of crystallized fatty acid, thus enabling a fatty acid solution in acetone to be obtained which contains the required quantity of vehicling or carrier sodium iodide; then the whole of the solution of flask A (1 cc) is taken and added in the flask sealed by a teflon membrane and containing the radioactive iodide in the dry state with a pH of 7. Then the sealed flask containing the radioactive iodide and the solution of fatty acids was placed in a dry water bath and heated at a temperature of 102°–103° C. for 5 minutes to perform the exchange reaction and obtain the fatty acid tagged with $I^{123}$. After heating, a venting needle was introduced into the teflon membrane closing the flask, in order to eliminate the acetone by evaporation. After this operation, 4 cc of the buffer solution was taken from the flask C and introduced into the flask containing tagged fatty acid; then the latter was placed in a dry water bath, subjecting the contents to agitation and heating for about 15 minutes at 70° C. to obtain a tagged fatty acid suspension. When the suspension had cooled, 1.5 cc of human albumin serum taken from the flask D was added; the solution then became limpid.

Before the preparation of the injectable solution, the tagging yield was determined, a tagged yield of 98.3% being obtained, corresponding to 1.7% of free radioactive iodide.

It will therefore be noted that operating with radioactive iodide in the dry state enables a better result to be obtained.

To verify this fact, various taggings were carried out on 16-iodo-9-hexadecenoic acid in the same conditions as before, but using aqueous solutions of radioactive iodide each having a total activity of 4 millicuries, but different volumes (30, 200 and 500 µl). The tagging yield was also determined. The results obtained are given in the following Table.

| Radioactive iodide (4 millicuries) | In the dry state | In 30 µl of solution | In 200 µl of solution | In 500 µl of solution |
|---|---|---|---|---|
| Tagging yield | 98.3% | 93.8% | 85.9% | 59.8% |

TABLE I

| Solution of NaI$^{123}$ | | Solution of fatty acid in acetone + vehicling NaI | | | | Heating | | |
|---|---|---|---|---|---|---|---|---|
| Volume (µl) | Total activity (mCi) | Volume (ml) | Concentration in fatty acid (mg/ml) | Molar ratio fatty acid/NaI | T(°C.) | Duration (min) | Tagging yield |
| 80 | 2 | 2.8 | 2.5 | 4.10$^2$ | 102–104 | 5 | 96.7 |

TABLE I-continued

| Solution of NaI[123] | | Solution of fatty acid in acetone + vehicling NaI | | | Heating | | |
|---|---|---|---|---|---|---|---|
| Volume (μl) | Total activity (mCi) | Volume (ml) | Concentration in fatty acid (mg/ml) | Molar ratio fatty acid/NaI | T(°C.) | Duration (min) | Tagging yield |
| 144 | 2 | 4 | " | " | " | " | 95.7 |
| 144 | 2 | 2.8 | " | " | " | " | 95.5 |
| 144 | 2 | 1 | " | " | " | " | 91.3 |
| 65 | 1 | 2 | " | " | " | " | 95 |

TABLE II

| Solution of NaI[131] | | Solution of fatty acid in acetone + vehicling NaI | | | Heating | | |
|---|---|---|---|---|---|---|---|
| Volume (μl) | Total activity (μCi) | Volume (ml) | Concentration in fatty acid (mg/ml) | Molar ratio fatty acid/NaI | T(°C.) | Duration (min) | Tagging yield |
| 10 | 10 | 0.5 | 4 | $7.7 \cdot 10^2$ | 99 | 5 | 95.4 |
| 20 | 20 | 0.5 | 4 | " | " | " | 94 |
| 25 | 25 | 0.5 | 4 | " | " | " | 92.3 |
| 30 | 30 | 0.5 | 4 | " | " | " | 90.9 |
| 40 | 40 | 0.5 | 4 | " | " | " | 86.9 |

What is claimed is:

1. A process for the preparation of a fatty acid tagged with radioactive iodine, wherein a non-radioactive fatty acid which is substituted in the omega position by an halogen selected from the group consisting of bromine and iodine is reacted with radioactive iodide in the dry state, in the presence of vehicling iodide, to exchange the bromine or iodine of such fatty acid for radioactive iodine.

2. A process according to claim 1, wherein the radioactive iodide in the dry state is obtained by evaporating an aqueous solution of said radioactive iodide having a pH of about 7.

3. A process for the preparation of a fatty acid tagged with radioactive iodine, wherein a non-radioactive fatty acid which is substituted in the omega position by an halogen selected from the group consisting of bromine and iodine is reacted with an aqueous solution of radioactive iodide, in the presence of vehicling iodide, to exchange the bromine or iodine of such fatty acid for radioactive iodine.

4. A process according to claim 3, wherein the aqueous solution of radioactive iodide has a pH of about 7.

5. A process according to claims 1, 2, 3, or 4, wherein the vehicling iodide is sodium iodide.

6. A process according to claim 1 or 3, wherein the starting material is an iodinated non-radioactive fatty acid.

7. A process according to claim 1, wherein the brominated or iodinated non-radioactive fatty acid is dissolved in a water-miscible ketone containing the vehicling iodide, and the solution of fatty acid is added to the radioactive iodide in the dry state.

8. A process according to claim 3, wherein the brominated or iodinated non-radioactive fatty acid is dissolved in a water-miscible ketone containing the vehicling iodide, and the solution of the non-radioactive fatty acid is added to the aqueous solution of radioactive iodide.

9. A process according to claim 3, wherein the aqueous solution of radioactive iodide has a volumetric activity of at least 20 millicuries per milliliter.

10. A process according to claim 1, wherein the radioactive iodide in the dry state has an activity such that the ratio between its activity in millicuries and the weight in milligrams of the brominated or iodinated non-radioactive fatty acid is at most 0.6.

11. A process according to claim 1 or 3, wherein the radioactive iodine is $^{123}$I.

12. A process according to claim 1 or 3, wherein after the exchange reaction, the ketone is evaporated and a radiochemically pure radioiodinated fatty acid is obtained without the necessity of a purification step, and then a slightly alkaline injectable buffer solution is added to form a colloidal suspension of tagged fatty acid, and such suspension is dissolved in a liquid compatible with the human body.

13. A process according to claim 12, wherein the liquid is human albumin serum.

14. A process according to claim 6, wherein the iodinated non-radioactive fatty acid has the formula:

$$I(CH_2)_{n'+1}-Y-(CH_2)_{n+1}-COOH,$$

where Y denotes the links $-CH_2-CH_2-$ or $-CH=CH-$ Z or E, and n and n' are integers from 3 to 10, and is prepared by condensing in liquid ammonia in the presence of lithium amide an omega-brominated acid having the formula:

$$BR-(CH_2)_{n+1}-COOH$$

and an acetylenic alcohol having the formula:

$$H-C\equiv C-(CH_2)_{n'}-CH_2OH,$$

to obtain omega-hydroxy-alkynoic acid having the formula:

$$HO-(CH_2)_{n'+1}-C\equiv C-(CH_2)_{n+1}-COOH,$$

and then subjecting the hydroxy omega alkynoic acid to reduction to obtain the corresponding omega-hydroxy-alkenoic acid or omega-hydroxy-alkanoic acid, reacting the omega-hydroxy-alkanoic acid or the omega-hydroxy-alkenoic acid thus obtained with paratoluene sulfonyl chloride to obtain the corresponding tosylated derivative, and subjecting the tosylated derivative thus obtained to a tosylate-iodine exchange reaction to obtain the corresponding iodized derivative.

15. A process according to claim 14, wherein the partial reduction of omega-hydroxy-alkynoic acid into Z omega-hydroxy-alkenoic acid is performed by hydrogenation in the presence of quinoline and by means of a catalyst with 5% palladium on calcium carbonate which has been deactivated at 95° C. by a lead acetate solution.

16. A process according to claim 14, wherein the partial reduction of omega-hydroxy-alkynoic acid into E omega-hydroxy-alkenoic acid is performed by means of sodium in solution in liquid ammonia, under pressure and at a temperature of 20° to 60° C.

17. A process according to claim 14, wherein the omega-hydroxy-alkynoic acid is totally reduced to obtain the corresponding omega-hydroxy-alkanoic acid by hydrogenation in the presence of a platinum catalyst.

18. A process according to claim 6, wherein the iodinated non-radioactive fatty acid has the formula:

$$I(CH_2)_{n'+1}-C\equiv C-(CH_2)_{n+1}-COOH$$

where n and n' are integers from 3 to 10 and is prepared by condensing in liquid ammonia in the presence of lithium amide a brominated fatty acid having the formula;

$$Br-(CH_2)_{n+1}-COOH$$

and an acetylenic alcohol having the formula:

$$H-C\equiv C-(CH_2)_{n'}-CH_2OH$$

to obtain omega-hydroxy-alkynoic acid having the formula:

$$HO-(CH_2)_{n'+1}-C\equiv C-(CH_2)_{n+1}-COOH$$

reacting the omega-hydroxy-alkynoic acid thus obtained with paratoluene sulfonyl chloride to obtain the corresponding tosylated derivative, and subjecting the tosylated derivative thus obtained to a tosylate-iodine exchange to obtain such iodized fatty acid.

19. A process according to claim 16, wherein the non-radioactive iodized fatty acid obtained is purified by high-performance liquid chromatography, using a silica-based support and an elution agent formed mainly by heptane, ether and acetic acid.

20. A process according to claim 18, wherein the non-radioactive iodized fatty acid obtained is purified by high-performance liquid chromatography, using a silica-based support and an elution agent formed mainly by heptane, ether and acetic acid.

* * * * *

UNITED STATES PATENT AND TRADEMARK OFFICE
CERTIFICATE OF CORRECTION

PATENT NO. : 4,476,106

DATED : October 9, 1984

INVENTOR(S) : Andre Bardy et al.

It is certified that error appears in the above—identified patent and that said Letters Patent is hereby corrected as shown below:

Column 1, line 27, change "and" to --for--;

Column 1, line 66, delete "to";

Column 3, line 24, change "disassociated" to --disassociation--;

Column 7, line 35, change "omega-hydroxy-alkanoic acids" to --omega-iodo-alkanoic acids--;

Column 7, line 40, change "acid" to --acids--;

Column 8, line 65, change " H--C C " to -- H--C$\equiv$C --;

Column 8, line 67, change " H--C C " to -- H--C$\equiv$C --;

Columns 11 and 12, under the heading "Elemental analysis - I - Obtained - change "30.42" to --32.42--;

Column 13, line 64, change "activity od resin" to --activity of resin--;

Column 18, line 51, change " C=C " to -- C$\equiv$C --.

Signed and Sealed this

Thirtieth Day of July 1985

[SEAL]

Attest:

DONALD J. QUIGG

Attesting Officer

Acting Commissioner of Patents and Trademarks